(12) United States Patent
Wironen et al.

(10) Patent No.: US 7,153,518 B2
(45) Date of Patent: Dec. 26, 2006

(54) PROCESSED SOFT TISSUE FOR TOPICAL OR INTERNAL APPLICATION

(75) Inventors: John F. Wironen, Gainesville, FL (US); Chris Seid, Gainesville, FL (US); Rebecca Jaw, Gainesville, FL (US); Thien Doan, Gainesville, FL (US); Gregg Ritter, Gainesville, FL (US); Russell S. Donda, Gainesville, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 348 days.

(21) Appl. No.: 10/228,558

(22) Filed: Aug. 27, 2002

(65) Prior Publication Data
US 2003/0104026 A1 Jun. 5, 2003

Related U.S. Application Data

(60) Provisional application No. 60/345,197, filed on Oct. 29, 2001, provisional application No. 60/324,399, filed on Sep. 24, 2001, provisional application No. 60/315,399, filed on Aug. 27, 2001.

(51) Int. Cl.
*A61F 2/10* (2006.01)
*A61K 9/10* (2006.01)
*A61K 35/36* (2006.01)

(52) U.S. Cl. ............ 424/422; 424/423; 424/DIG. 13; 424/572

(58) Field of Classification Search ............ 424/422, 424/423, 400, DIG. 13, 572
See application file for complete search history.

(56) References Cited

U.S. PATENT DOCUMENTS

| | | | | |
|---|---|---|---|---|
| 5,314,874 | A | * | 5/1994 | Miyata et al. ............. 514/21 |
| 5,356,629 | A | * | 10/1994 | Sander et al. ............ 424/422 |
| 5,665,391 | A | * | 9/1997 | Lea ......................... 424/484 |
| 5,810,801 | A | * | 9/1998 | Anderson et al. ........... 606/9 |

* cited by examiner

*Primary Examiner*—Edward J. Webman
(74) *Attorney, Agent, or Firm*—McAndrews, Held & Malloy

(57) ABSTRACT

Disclosed herein are novel injectable, biocompatible compositions, preferably, comprising a combination of particulate, processed tissue and a carrier. Specifically disclosed are compositions comprising acellular, pulverized dermis combined with at least one glycosaminoglycan and/or gelatin. The subject compositions provide for improved retention of the composition at the site of implantation. Also disclosed are medical applications using the disclosed compositions, such as cosmetic enhancement or filling in of voids due to abnormalities, injuries, surgery, or aging. In addition, kits comprising at least one container of a freeze-dried, particulate tissue and at least one container of a glycosaminoglycan, or crude platelet extract and used thereof as a wound treatment/dressing, are disclosed.

23 Claims, No Drawings

PROCESSED SOFT TISSUE FOR TOPICAL OR INTERNAL APPLICATION

This application is related to and claims priority from each of the following U.S. provisional patent applications: U.S. Ser. No. 60/345,197, filed Oct. 29, 2001; U.S. Ser. No. 60/324,399, filed Sep. 24, 2001; and U.S. Ser. No. 60/315,399, filed Aug. 27, 2001.

BACKGROUND OF THE INVENTION

In recent years, the cosmetic and medical uses of collagen materials have increased dramatically. For example, collagen compositions are now commonly used in facial enhancement procedures such as augmentation of the lips or filling in of wrinkles via collagen injection. Collagen is also used to fill voids in the face resulting from the removal of skin cancers such as basal cells or melanoma. U.S. Pat. Nos. 5,527,856; 5,550,187; and 5,752,974 relate to collagen compositions for various applications. Medical procedures using collagen have also been developed to increase the competency of sphincter muscles located throughout the body, which involves injection of collagen directly into the sphincter muscles. U.S. Pat. No. 5,490,984. This technique has been shown to alleviate anorectal and/or urinary incontinence.

Despite its recognized benefits, the use of collagen in medical applications is not without drawbacks. First, there is only a limited supply of useful collagen, as it must be procured from a xenogenic and/or allogenic donor. With respect to xenogenic collagen, it has been shown to induce an acute antigenic response, which can cause deleterious symptoms in the recipient and ultimately leads to the rapid rejection of the collagen material. While, allogenic collagen has been shown to have a lower rejection rate, it does not retain its shape well and still is ultimately absorbed. In sum, the medical/cosmetic uses of collagen typically only provide a temporary result.

Accordingly, efforts are being made to develop injectable collagen based materials that are not rejected and which have increased retention in the body and a lower absorption rate than current commercially available products.

SUMMARY OF THE INVENTION

The subject invention is directed to a biomaterial composition comprising a combination of processed tissue and a carrier. The processed tissue may by intact or in particulate form. The term "tissue" as used herein includes, but is not limited to, allogenic or xenogenic bone, neural tissue, fibrous connective tissue including tendons and ligaments, cartilage, dura, fascia, pericardia, muscle, heart valves, veins and arteries and other vasculature, dermis, adipose tissue, or glandular tissue. According to one aspect, the subject composition is preferably flowable and thermoplastic, and has increased retention in the body, while possessing a decreased rate of rejection. The subject invention also pertains to kits comprising a container freeze-dried, pulverized tissue (preferably dermis) and a container of a rehydrating fluid.

These and other advantageous aspects of the subject invention are described in further detail below.

DESCRIPTION OF THE ILUSTRATIVE EMBODIMENTS

In one embodiment, the subject invention relates to a composition comprising pulverized, acellular human tissue and a carrier, preferably gelatin and/or one or more glycosaminoglycans. It is preferred that the glycosaminoglycans be of a concentration to aid in wound healing, and/or reduction in scar formation. The subject biomaterial composition can be freeze-dried to prolong shelf-life. The tissue may be allogenic or xenogenic or comprise a combination of particles from both allogenic and xenogenic sources.

The invention also pertains to methods for completely or partially blocking, augmenting, sealing, or filling various lumens or voids within the body of a patient. The term "void" is intended to encompass any hollow space created by congenital abnormalities, disease, aging, injury and/or surgery, such as extraction of tumors and other growth masses. As such, the term "void" encompasses lesions, fissures, fistulae, cysts, diverticulae, aneurysms, and any other undesirable void present in any tissue or organ of the body which may result from congenital abnormalities, disease, aging, injury or surgery. For example, the methods of the invention can be used to seal fissures or crevices within a tissue or structure (such as a vessel), or junctures between adjacent tissues or structures, to prevent the leakage of blood or other biological fluids. As used herein, the term "lumen" is intended to encompass various hollow organs or vessels of the body, such as Fallopian tubes, veins, arteries, intestines, trachea, and the like.

According to further embodiment, the subject invention is directed to kits that comprise an amount of acellular, particulate tissue, and a separate amount of a carrier, wherein both are provided in an appropriate container (e.g., a syringe or vial). The acellular particulate tissue is preferably freeze-dried and provided in a syringe. The carrier is preferably in an aqueous solution and/or suspension in a vial. In an alternative method, the tissue particulate and the carrier are contained in individual syringes. Immediately prior to use, the syringes are connected and the contents of each are mixed back and forth, such as in the system described in WO 01/47571. Furthermore, the subject kit comprises a container comprising a hemostatic agent. Examples of a suitable hemostatic agent include collagen, nonsoluble polysaccharide, fibrin, fibrinogen, chitosan, cellulose and dried gelatin. Alternatively, the hemostatic agent is pulverized tissue. Preferably collagen (see e.g. U.S. Pat. No. 6,027,471) is the hemostatic agent. The collagen is preferably provided in powder form. Those skilled in the art will appreciate that the kits are advantageous for use in the field to treat traumas, where immediate surgical attention is not available, or for surgeries conducted in a controlled operating room environment, including use in cosmetic surgeries.

When using hyaluronic acid or salts thereof (HA) as carrier it is preferably provided as an aqueous solution comprising about 0.01 percent to about 10 percent, by weight. Preferably still, the HA is provided as an aqueous solution comprising about 0.5 percent to about 5 percent HA, by weight. When using chondroitin sulfate as a carrier, it preferably is provided as an aqueous solution comprising about 1 percent to about 30 percent chondroitin sulfate, by weight. In another embodiment, the chondroitin sulfate is provided as an aqueous solution comprising 1 percent to 15 percent chondroitin sulfate by weight.

According to the most general method of the invention, an effective amount of a biomaterial composition is administered to the site of a lumen or void within the body of a patient. The term "effective amount", as used herein, means the quantity of biomaterial needed to augment, block, or fill the biological structure of interest. The effective amount of biomaterial administered to a particular patient will vary depending upon a number of factors, including: the sex, weight, age, and general health of the patient; the patient's own ability to absorb or break down the biomaterial; the type, concentration, and consistency of the biomaterial; and the particular site and condition being treated. The biomaterial may be administered over a number of treatment sessions.

As described above, an effective amount of one or more biologically active agents, such as a wound healing agent, antibiotic, or antimicrobial agent, can be incorporated into the biomaterial composition. In this context, an "effective amount" refers to the amount of biologically active agent, antibiotic, or antimicrobial agent required to obtain the desired therapeutic effect, such as improved or accelerated healing of the defect or void, or prevention of infection at the site of administration.

"Biologically active agent" as used herein includes, but is not limited to, antiviricides, particularly those effective against viruses such as HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin, etc.; amino acids, magainins, peptides, vitamins, inorganic elements, co-factors for protein synthesis; hormones; endocrine tissue or tissue fragments; enzymes such as collagenase, peptidases, oxidases, etc.; polymer cell scaffolds with parenchymal or other cells; surface cell antigen eliminators; angiogenic or angiostatic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, growth factors, growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; bioerodable polymers such as those disclosed in U.S. Pat. Nos. 4,764,364 and 4,765,973; glycosaminoglycans such as hyaluronic acid, chondroitin sulfate, dermatan sulfate, heparin sulfate and the like, and combinations of any of the foregoing. The amounts of such medically useful substances can vary widely with optimum levels being readily determined in a specific case by routine experimentation.

The carrier component of the composition is important for providing some of the desired attributes such as flowability and thermoplasiticity. Aqueous suspensions/solutions of gelatin, hyaluronic acid and/or chondroitin sulfate are preferred carriers. PCT publications WO 98/40113 and WO 99/38543 are cited herein for examples of a gelatin carrier suitable for use in the subject composition. In addition, it is to be understood that other carrier agents are suitable for use in the subject composition, including, but not limited to, proteoglycans and GAGs (such as chondroitin sulfate, heparin sulfate, dermatan sulfate, hyaluronic acid, keratan sulfate and the like), polyethylene glycols and other similar hydrophillic polymers, PLURONIC® polyoxyethylene detergents, collagen, algins, chitosan, glycerol, or combinations thereof.

In a specific embodiment, the subject composition comprises pulverized dermis combined with gelatin mixed in a liquid (e.g water or blood), wherein the gelatin comprises about 10 to about 30 percent, by weight, of the composition. In a preferred embodiment the gelatin comprises 12 to 24 percent of the composition. In an alternative embodiment, the subject composition comprises pulverized dermis combined with hyaluronic acid in a liquid wherein the hyaluronic acid comprises 0.5 to 5 percent, by weight, of the composition. In a preferred embodiment, the hyaluronic acid comprises 1 to 3 percent, by weight of the composition. Those skilled in the art will readily and routinely determine the appropriate concentrations of the carrier for a given purpose.

The term "growth factor" as used herein refers to a polynucleotide molecule, polypeptide molecule, or other related chemical agent that is capable of effectuating differentiation of cells. Examples of growth factors as contemplated for use in accord with the teachings herein include a epidermal growth factor (EGF), transforming growth factor-alpha (TGF-alpha), transforming growth factor-beta (TGF-beta), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), and/or platelet derived growth factor (PDGF).

As used herein, the term "effective amount", whether in reference to a biomaterial or biologically active agent, also refers to that amount of material which is pharmaceutically and physiologically acceptable to the particular patient undergoing treatment.

The methods provided by this invention relate to the administration of a biomaterial to fill in whole, or in part, any void spaces formed as the result of surgical, chemical or biological removal of unnecessary or undesirable growths, fluids, cells, or tissues. The biomaterial can be locally administered at the site of the void, augmenting the remaining and surrounding tissue to aid in the healing process and to minimize infection. This augmentation is especially useful for void sites created after tumor excision, such as after breast cancer surgery, surgery for removal of tumorous connective tissue, bone tissues or cartilage tissue, and the like.

The invention also provides methods for treating undesired lesions, fissures, diverticulae, cysts, fistulae, aneurysms, and any other undesirable void present within the body of a patient, by administering a biomaterial to the site of these conditions. For example, the biomaterial can be injected, implanted, or threaded into fistula between viscera or into the opening or orifice from a viscus to the exterior of the patient's body. The biomaterial fills the defect formed by these pathological states and stimulates fibroblast infiltration and healing, resulting in the ingrowth of tissue.

In addition, the subject biomaterials can be used in accord with conventional cosmetic techniques for enhancing, augmenting or otherwise altering the structure of the face and other areas of the body. For example, they may be injected directly into the lips to provide a fuller appearance. Moreover, the subject biomaterials can be injected to fill in and lessen the appearance of wrinkles. Further, they may be injected to other areas of the face and body for purposes of augmenting or enhancing the injected portion.

The biomaterial can be introduced by injection through a small gauge needle into one of the fistular orifices, filling all of the branches of the orifice and polymerizing or crosslinking in situ. Alternatively, dehydrated strings or rods of the materials (prepared as previously described) can be threaded into the lesions through an orifice or introduced by catheter. Various types of fistulae can be treated by this method and include anal fistulae, arteriovenous fistulae, bladder fistulae, carotid-cavernous fistulae, external fistulae, gastric fistulae, intestinal fistulae, parietal fistulae, salivary fistulae, vaginal fistulae, anorectal fistulae, and the like.

Diverticulae also can be treated by the methods of the invention. These abnormal physiological structures are pouches or sac openings from a tubular or saccular organ, such as the intestine, the bladder, and the like, and can be filled or augmented by the biomaterial. Cysts, which are abnormal sacs with a membrane lining containing gas, fluid, or semi-solid material, also can be filled, along with pseudocysts, which are an accumulation of fluid in a cyst-like locule, but without an epithelial or other membranous lining. Examples of cysts that can be treated by the invention include serous cysts, sebaceous cysts, dermoid cysts, bone cysts, and the like.

In a specific embodiment, a composition of gelatin, processed dermis and PDGF is topically administered to a void or other defect as a dressing to initiate regeneration of skin. Preferably, PDGF is provided in a purified form or partially purified form such as in a crude platelet extract (CPE) obtained from platelet rich plasma. For example, CPE is obtained by the method disclosed in copending application U.S. Ser. No. 09/776,619, which is provided here in brief: (a) obtain outdated apheretically purified platelets (platelets present in 60–70 ml plasma; (b) keep platelets at 40° C.; (c) combine donor platelets into 500 ml centrifuge tubes; (d) centrifuge tubes at 8000×g 20 minutes at 4° C.; (e) remove plasma; (f) add 20 volumes of ice cold sterile saline to platelets and gently resuspend pellet; (this step is to remove as much plasma/serum components as possible); (g) re-centrifuge at 8000×g 20 min at 4° C. to repellet platelets; (h) to platelet pellet, add 10 volumes extraction buffer (1. 45% Ethanol containing 150 ul concentrated HCl for every 50 ml of solution; or 2. 100 mM $NaH_2PO_4$; 1.5M NaCl; pH 7.4) and agitate overnight at 4° C. (12–16 hours); (i) pellet lysed platelet material by centrifugation at 12,000 rpm 20 minutes 4° C.; (j) remove platelet extract, referred to as crude platelet extract.

According to a further embodiment, the subject invention pertains to compositions for topical application to treat wounds, burns, lesions, ulcers, sores, cuts, abrasions and the like. Preferably, the topical compositions comprise one or more glycosaminoglycans including, but not limited to, hyaluronic acid, chondroitin sulfate and dermatan sulfate. In a preferred embodiment the glycosaminoglycan (GAG) is combined with crude platelet extract, such as that obtained from the specific methods outlined above. Alternatively, a topical composition comprises CPE without necessarily being combined with a GAG component. The viscosity of the foregoing compounds is adjusted to suit a given purpose, such as by increasing or decreasing the amount of GAG or percentage of water present in the compounds.

In addition, to applying a GAG and/or CPE mixture as a topical, such compositions can be used to treat internal wounds, injuries, and defects as well. Furthermore, such compositions can be used in association with autograft, allograft, and xenograft tissue implants. Implants can be infused, dipped, coated, etc. in such compositions to increase healing and/or remodeling of the implanted tissue. The term "infused" as used herein relates to its broad definition and included dipping, coating, adhering, infusing or any other mode of associating a substance with an implant. For example, a bone implant can be coated with such composition prior to surgery to aid in the remodeling of the implant at the site of implantation.

Stem cells are gaining ever-increasing recognition for their beneficial uses in the treatment of injuries and disease. According to another embodiment, stem cells are stored or treated with a mixture of one or more GAGs. The GAG content acts a preservative or to stimulate the activity of the stem cells upon internal or topical administration. The use of a GAG composition as a preservative or supercharger improves the effectiveness of the stem cells upon administration. In a preferred embodiment, stem cells are stored in a media containing hyaluronic acid and/or chondroitin sulfate and then applied to an internal or topical site of need.

In an alternative embodiment, the subject methods are useful for a reversible form of birth control or sterility in females, wherein the biomaterial is threaded, injected, or implanted, such that the Fallopian tubes are filled or blocked by the biomaterial, thereby preventing egg and/or sperm from passing through or around the biomaterial. Using this approach, pregnancy would be prevented since the ova or eggs located in the Fallopian tubes would not exit to the uterus and would not make contact with sperm. The blockage, and hence the sterility or birth control, is reversible by removal of the biomaterial or resectioning of the tube after surgery, wherein the blocked portion of the tube is excised and the remaining portions of the tube are reconnected. It is preferable that the sections of the Fallopian tubes blocked with the biomaterial are those directly connected or closest to the uterus. Administration of the biomaterial for this therapeutic indication can occur via catheter or via endoscopes, such as a fiberoptic scope, hysteroscope, and the like. See "Hysteroscopic Approaches for Tubal Closures," John J. Sciarra, Research Frontiers in Fertility Regulation, 1980, Chapter 26, pp. 270–286. Preferably, the biomaterial is injected into the Fallopian tubes using a catheter.

The delivery of the biomaterial via injection or implantation provides a means to effectively target the biomaterial to a specific site or location, thereby localizing the biomaterial and minimizing systemic side effects. In addition, the biocompatibility of the material minimizes any immunologic reaction of the patient to the biomaterial. Moreover, the administration of the biomaterial via implant or injection is minimally invasive and usually can be performed on an outpatient basis, resulting in a lower cost than other surgical forms of sterility or birth control. The procedure also eliminates patient compliance, since the patient need not follow any specific instructions or remember to ingest or insert other forms of birth control, such as pills, diaphragms, and the like. However, supplemental forms of birth control can be utilized, if desired, especially those which prevent disease transmission.

The biomaterial and the methods of the invention also can be utilized for tracheal occlusions for in utero correction of fetal congenital defects, such as child congenital diaphragmatic hernia (CDH). See Longaker et al., "Maternal Outcomer AFter Open Fetal Surgery: A Review of the First 17 Human Cases", J. Amer. Med. Assoc., 265(6):737–741 (1991). CDH primarily induces pulmonary hypoplasia, thereby lessening the ability of a newborn to adequately exchange oxygen. The condition is typically diagnosed by ultrasound during pregnancy and is caused by the compression of the developing lungs by other internal organs, such as the intestine, stomach, and liver, due to the herniation of the diaphragm. The rapture of the diaphragm allows the internal organs to move into the chest cavity, restricting the development of the lungs, since there is less space for lung growth.

By occluding the fetal trachea, the intrapulmonary pressure gradually increases due to the fluid build-up in the lungs. This pressure increase propels the internal organs slowly from the chest cavity and allows full development of the fetal lungs, preventing pulmonary hypoplasia.

It is desirable that the occlusion method be easily reversible at birth, so that the infant can breathe without difficulty. Fortunately, the umbilical connection between mother and child provides sufficient time to remove the occlusion before the infant must breathe on its own. It is important that the tracheal occlusion method be reproducible, reliable, reversible, and atraumatic, thereby minimizing the risk to the mother and infant both at the time of occlusion and upon removal of the biomaterial, which causes the occlusion. Further, the cell lining of the trachea or the trachea itself must not be severely damaged.

Administration of the biomaterial to the fetal trachea can be via injection, using the ultrasound technique or fiberoptic scope for placement guidance. The biomaterial is placed within the trachea to completely fill it, forming a column of material. Preferably, a suture or stitch is placed through the trachea to hold the biomaterial in place. Since the trachea will expand in size as the fetus matures, it is important to utilize a biomaterial that expands such that the trachea continues to be blocked and the biomaterial is not expelled. Therefore, the preferred biomaterial for this indication will be one that is strongly hydrophilic and can expand at a rate that is equal to the growth rate of the fetal trachea. Methods for increasing the hydrophilicity of a biomaterial composition are described in the previous section.

This method of administration minimizes the surgical risks to the mother and the fetus when compared to other occlusion approaches, such as physically tying off the trachea (see Longaker). It also allows for easy removal, since the biomaterial typically gels and solidifies in situ and can easily be removed with tweezers or similar instruments. This quick and easy removal process lessens the time of non-breathing for the newborn infant. In order to optimize the timing of the birth and to facilitate the biomaterial's removal, the delivery is typically by Caesarean section.

Furthermore, the subject methods can be used to treat incontinence due to incompetent sphincter muscles along the GI and urinary tracts. Treatment involves the injection of the subject compositions directly into the sphincter muscles.

For all the various therapeutic indications that can be treated using the methods of the invention, it is desirable to properly place the biomaterial in the bodily region of interest, such that the biomaterial either is held in place during performance of the method, or held in place for a sufficent length of time to allow polymerization in situ for certain biomaterials. As described above, the subject biomaterials are preferably thermoplastic, wherein the biomaterials gel at a given temperature (e.g. preferably body temperature) which acts to keep the biomaterial at the site of need.

Separately, or in conjunction with the thermoplasticity, the novel thermoplastic characteristics of the subject biomaterials, the biomaterial can be further localized by the use of a clamp, balloon catheter, umbrella, surgical instrument, and the like. Injection of a biomaterial between a dual balloon catheter can be used to block the lumen anterior and posterior to the catheter tip.

Moreover, there are procedures in which the ultimate removal of the biomaterial is desired or necessary. The biomaterial also can be pulled from a lumen using strings, wires, and the like, which are firmly embedded or attached to the biomaterial in order to permit complete removal.

An alternative method for removal is the in vivo degradation of the biomaterial, for example, by enzymes such as collagenase. The rate of degradation in vivo and eventual resorption by the body can be controlled by varying a number of factors including, without limitation, the type and concentration of collagen used.

Furthermore, the biomaterial may include analgesics known in the art. For example, the subject composition can include buprenorphine, morphine, and other opiates, non-steroidal anti inflammatory agents such as acetomenophen, ibuprophen, aspirin and the like, and/or steroids. Adding such compounds will assist in alleviating pain subsequent to surgery and help keep inflammation down.

EXAMPLES

Example 1

Production of Acellular, Thermoplastic, Dermis Composition

Dermis tissue is procured and prepared according to the methods set forth in co-pending application Ser. No. 60/296, 530 (incorporated herein by reference) to produce acellular, viral inactivated dermis tissue. Prior, concurrent, or subsequent to this processing, dermis tissue may be treated in accord with the teachings of PCT publications WO 00/29037 and WO 01/08715. The dermis tissue is then pulverized preferably by cryofracturing. Pulverization by cryofracturing involves the steps of cooling a segment of the acellular dermis to a temperature wherein it is brittle. Suitable temperatures are generally about $-10°$ F. but temperatures as low as $-100°$ F. can also be utilized. Suitable low temperatures can be achieved utilizing liquid nitrogen, alcohol with solid carbon dioxide, acetone with solid carbon dioxide, and the like. The low cooling permits the skin to be pulverized using standard procedures including mortar and pestle or cryogenic grinding and freeze drying such as with a freezer mill sold by Spex Industries, Inc. of Edison, N.J. under the trademark SPEX 6700 Freezer/Mill. Pulverization results in dermis particles, which are then freeze-dried with or without being mixed with a carrier. Preferably, gelatin is combined with the dermis particles and then freeze-dried.

Alternatively, the acellular dermis can be pulverized by means of ultrasonic disruption. According to this method, an ultrasonic processor, such as sold under the trademark VIBRA CELL by Sonico and Materials, Inc. of Danbury Conn. can be used. According to the procedure of ultrasonic disruption, an ultrasonic power supply (generator) converts 50/60 Hz line voltage to high frequency 20 KHz (20,000 cycles per second) electrical energy is transmitted to a piezoelectric transducer within a converter, where it is changed to mechanical vibrations. The vibrations from the converter are intensified by a probe creating pressure waves in a liquid. This action forms millions of microscopic bubbles which expand during a negative pressure excursion, and implode violently during a positive excursion. It is this action, referred to as cavitation, which produces the powerful shearing action and causes the molecules in the liquid to become intensely agitated. Using a acid solution in the ultrasonic processor allows denaturization and extraction of the collagen to occur.

Example 2

Preparation of Dermis Composition for Injection

Reference is made to copending application Ser. No. 09/474,276 filed Dec. 29, 1999 (whose teachings are incorporated by reference) for a kit comprising a first 5 cc syringe containing 1 ml of reconstitution fluid and a second syringe containing 3 mg of the dermis composition prepared by Example 1. The dermis composition is reconstituted by repeated transfer between the first and second syringes thereby mixing with the reconstitution fluid to form a flowable paste. It is to be understood that for some purposes the paste is preferably moldable. Unless specified differently, reconstitution fluid, rehydrating fluid and rehydrating solution are used interchangeably herein, and are intended to relate to any fluid for rehydrating freeze-dried tissue, and can include solutions or suspensions. The two syringes are disconnected and the syringe containing the paste is used to inject at a site of need. Preferably, the dermis is reconstituted with a suspension/solution comprising CPE, GAG, or both.

Example 3

Sheet of Acellular, Processed Tissue Infused with One or More Glycosaminoglycans In a further, alternative embodiment, a sheet or piece of freeze-dried, acellular processed tissue is obtained, preferably as produced according to the teachings of co-pending application Ser. No. 60/296,530 (incorporated herein by reference), and is then rehydrated with glycosaminoglycan solution. The rehydrated tissue sheet can be applied to a wound such as a burn, cut, scrape, bite and the like. In a another embodiment, the subject invention pertains to a kit comprising one or more pieces of acellular processed tissue, preferably freeze-dried, and a container of a rehydrating solution. The rehydrating solution/fluid preferably comprises at least one glycosaminoglyan. The kit also may comprise a container comprising an amount of a hemostatic agent. The kits are advantageous for use in the field to treat traumas, where immediate surgical attention is not available, or for surgeries conducted in a controlled operating room environment, including plastic surgery.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An implantable composition comprising an admixture of a carrier and acellular, pulverized dermis tissue, wherein said dermis tissue is allogenic or xenogenic, or both, wherein said carrier is a gelatin and wherein said gelatin comprises about 10 to about 30 percent, by weight, of said composition.

2. The implantable composition of claim 1, wherein said composition is injectable and thermoplastic.

3. The implantable composition of claim 1 further comprising at least one biologically active agent.

4. The implantable composition of claim 3, wherein said biologically active agent is an antiviricide effective against HIV and hepatitis; an antimicrobial and/or antibiotic selected from the group consisting of erythromycin, bacitracin, neomycin, penicillin, polymyxin B, tetracycline, viomycin, chloromycetin, streptomycin, cefazolin, ampicillin, azactam, tobramycin, clindamycin and gentamycin or a growth factor or a combination of any of the foregoing.

5. The implantable composition of claim 3 wherein said biologically active agent is a growth factor.

6. The implantable composition of claim 5 wherein said growth factor is epidermal growth factor (EGF), transforming growth factor-alpha (TGF-alpha), transforming growth factor-beta (TGF-beta), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), or platelet derived growth factor (PDGF), or a combination of the foregoing.

7. The implantable composition of claim 6 wherein said growth factor is PDGF.

8. An implantable composition comprising an admixture of a carrier and acellular, pulverized dermis tissue, wherein said dermis tissue is allogenic or xenogenic, or both, wherein said carrier is hyaluronic acid, and said hyaluronic acid comprising about 0.5 to about 5 percent of said composition.

9. A kit comprising a first syringe containing an amount of a reconstitution fluid and a second syringe comprising an admixture of freeze-dried acellular, pulverized dermis, gelatin and a carrier selected from the group consisting of hyaluronic acid and chondroitin sulfate, wherein when the contents of the first syringe and the second syringe are combined to provide a reconstituted composition, the gelatin comprises 10% to 30% by weight of reconstituted composition, the hyaluronic acid comprises 0.5 to 5 percent by weight of said reconstituted composition and the chondroitin sulfate comprises 1% to 30% by weight of said reconstituted composition.

10. The composition of claim 1 further comprising an analgesic.

11. The composition of claim 10, wherein said analgesic is buprenorphine, morphine, an opiate, a nonsteroidal anti-inflammatory agent or a combination thereof.

12. A kit comprising at least one container containing an amount of acellular, particulate dermis and at least one container comprising an aqueous carrier solution, wherein said aqueous carrier solution comprises at least one glycosaminoglycan selected from the group consisting of hyaluronic acid, chondroitin sulfate and a mixture thereof, wherein said hyaluronic acid comprises 0.5 to 5 percent by weight of said solution, and wherein said chondroitin sulfate comprises 1 percent to 15 percent by weight of said solution.

13. The kit of claim 12 wherein said at least one container containing an amount of acellular, particulate dermis and/or said at least one container containing an aqueous carrier solution is a syringe or vial.

14. The kit of claim 13 wherein said at least one container containing an amount of acellular, particulate dermis is a 0.5 CC syringe.

15. A piece of acellular, dermis infused with a solution comprising one or more glycosaminoglycans, wherein said one or more glycosaminoglycans are selected from the group consisting of hyaluronic acid and chondroitin sulfate, wherein said hyaluronic acid comprises 0.5 to 5 percent by weight of said infused dermis, and wherein said chondroitin sulfate comprises 1 percent to 15 percent by weight of said infused dermis.

16. The piece of acellular, dermis of claim 15, wherein said piece of acellular dermis is in sheet form.

17. The piece of acellular, dermis of claim 15, wherein said one or more glycosaminoglycans comprises hyaluronic acid, or a salt thereof, chondroitin sulfate, or a combination thereof.

18. The kit of claim 12, further comprising a separate container containing an amount of a hemostatic agent, optionally, said hemostatic agent is combined with the acellular, particulate dermis.

19. The kit of claim 18, wherein said hemostatic agent is collagen, fibrin, fibrinogen, chitosan, cellulose, gelatin, or a combination thereof.

20. The kit of claim 19, wherein said hemostatic agent is powdered collagen.

21. A kit comprising a first container comprising freeze-dried, pulverized dermis and a second container comprising a reconstitution solution, wherein said reconstitution solution comprises hyaluronic acid at a concentration of from about 0.5 percent to about 5 percent by weight of said solution, or chondroitin sulfate at a concentration of from about 1 percent to about 15 percent by weight of said solution, or a combination thereof.

22. The kit of claim 21 wherein said reconstitution solution comprises said hyaluronic acid.

23. The kit of claim 21, wherein said dermis is allogenic or xenogenic.

* * * * *